US010716660B2

(12) United States Patent
King et al.

(10) Patent No.: US 10,716,660 B2
(45) Date of Patent: Jul. 21, 2020

(54) ENDOGRAFT FOR TREATING BRANCHED VESSELS

(71) Applicant: COOK MEDICAL TECHNOLOGIES LLC, Bloomington, IN (US)

(72) Inventors: Chantelle King, Queensland (AU); Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/228,438

(22) Filed: Aug. 4, 2016

(65) Prior Publication Data
US 2018/0036110 A1 Feb. 8, 2018

(30) Foreign Application Priority Data

Aug. 4, 2016 (AU) .................. 2016210717

(51) Int. Cl.
*A61F 2/07* (2013.01)
*A61F 2/06* (2013.01)
*A61F 2/89* (2013.01)

(52) U.S. Cl.
CPC ................... *A61F 2/07* (2013.01); *A61F 2/89* (2013.01); *A61F 2002/061* (2013.01);
(Continued)

(58) Field of Classification Search
CPC .......... A61F 2002/065; A61F 2002/072; A61F 2002/30172; A61F 2/07
See application file for complete search history.

(56) References Cited

U.S. PATENT DOCUMENTS 6,645,242 B1 * 11/2003 Quinn .................. A61F 2/07
623/1.13
7,537,606 B2 5/2009 Hartley et al.
(Continued)

FOREIGN PATENT DOCUMENTS

EP      2547287 A1    1/2013
WO   WO 03/082153 A2  10/2003
WO   WO 2006/065644 A1  6/2006

OTHER PUBLICATIONS

Patent Examination Report No. 1 for corresponding AU 2016210717 dated Sep. 30, 2016, 4 pages.
(Continued)

*Primary Examiner* — Christopher D. Prone
(74) *Attorney, Agent, or Firm* — Brinks Gilson & Lione

(57) ABSTRACT

An endograft comprising a proximal end and a distal end is disclosed. The endograft includes a tube of biocompatible material. The tube includes a main lumen extending longitudinally from the proximal end to the distal end, the main lumen including a proximal portion, an intermediate portion and a distal portion; a branch lumen within the intermediate portion of the main lumen; and a seam, the seam extending longitudinally beside both the branch lumen and the distal portion of the main lumen, wherein the tube includes a lateral cross-section defining a tubular wall pinched together by the seam to form a branch portion. The branch portion includes an entrance within the intermediate portion of the main lumen and an exit through the tubular wall of the main lumen.

14 Claims, 9 Drawing Sheets

(52) U.S. Cl.
CPC ... *A61F 2002/065* (2013.01); *A61F 2002/075* (2013.01); *A61F 2210/0014* (2013.01); *A61F 2230/0067* (2013.01); *A61F 2250/0039* (2013.01); *A61F 2310/00023* (2013.01)

(56) References Cited

U.S. PATENT DOCUMENTS

| | | |
|---|---|---|
| 8,394,136 B2 | 3/2013 | Hartley et al. |
| 8,906,086 B2 | 12/2014 | Roeder et al. |
| 9,101,501 B2 | 8/2015 | Laborde et al. |
| 9,125,764 B2 | 9/2015 | Shaw et al. |
| 9,155,611 B2 | 10/2015 | Sun |
| 2005/0131518 A1* | 6/2005 | Hartley ............... A61F 2/07 623/1.13 |
| 2011/0276062 A1 | 11/2011 | Bolduc |
| 2014/0081385 A1 | 3/2014 | McAllister et al. |
| 2015/0148884 A1 | 5/2015 | Douglas |

OTHER PUBLICATIONS

European Search Report for EP Application No. 17275120, dated Dec. 15, 2017, 7 pages.

\* cited by examiner

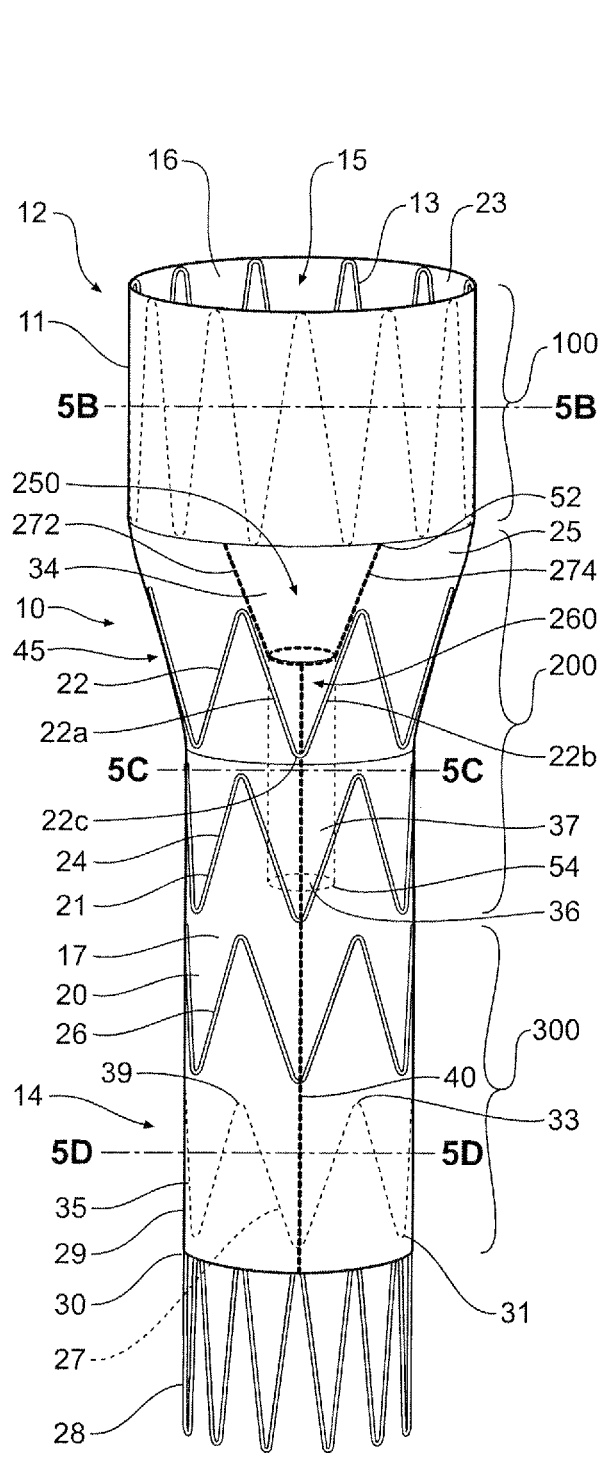
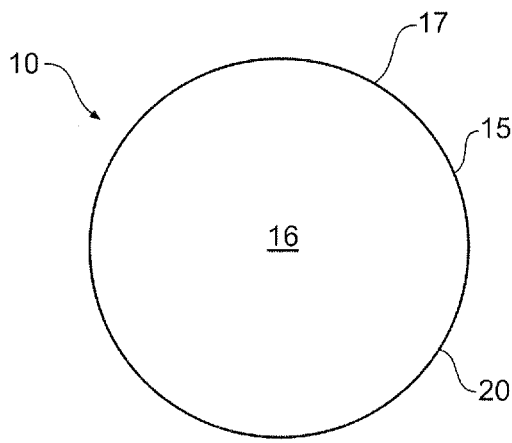
Figure 5B
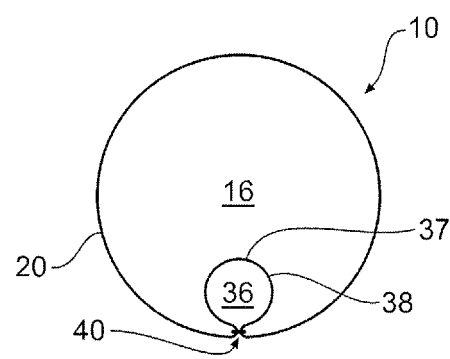
Figure 5C
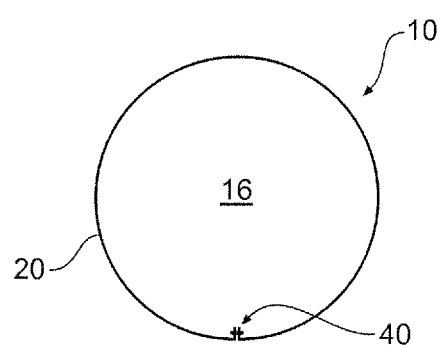
Figure 5D
Figure 5A

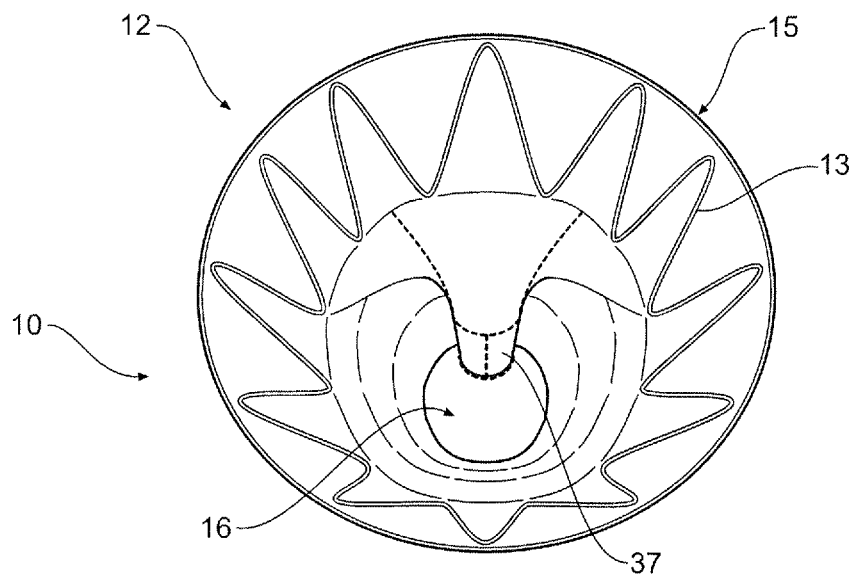
Figure 7
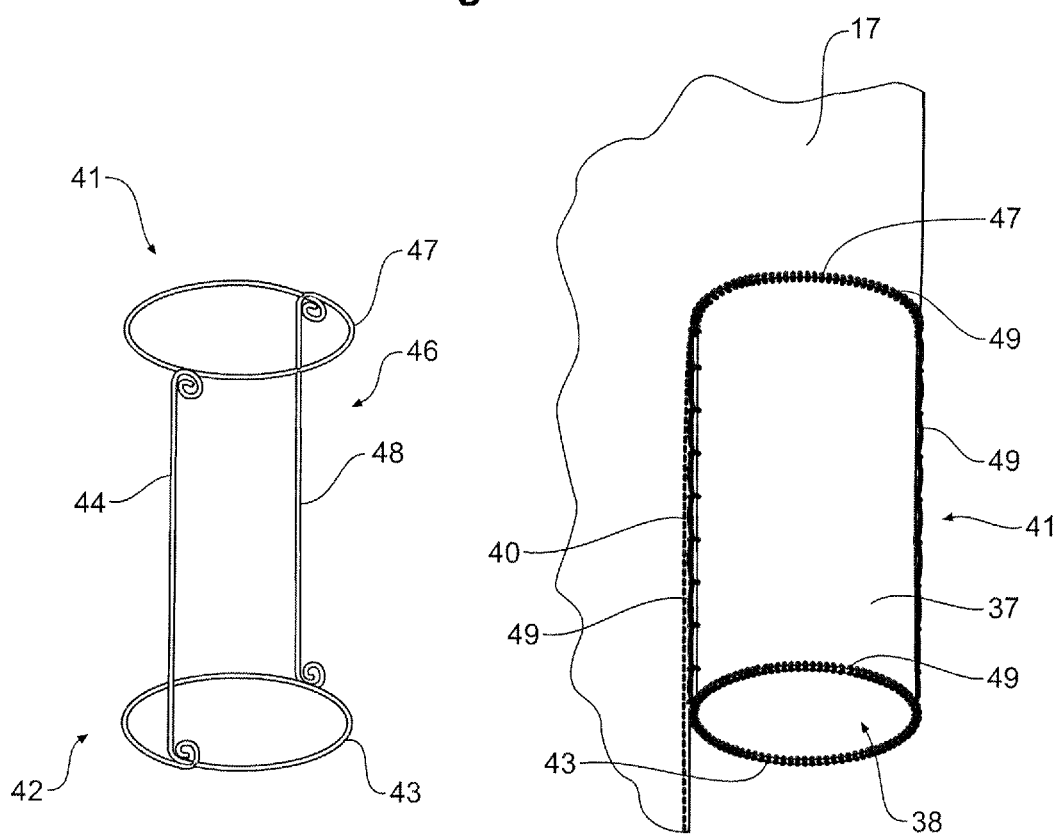
Figure 8
Figure 9

ENDOGRAFT FOR TREATING BRANCHED VESSELS

CROSS-REFERENCE TO RELATED APPLICATIONS

The present patent document claims the benefit of priority to Australian Patent Application No. 2016210717, filed Aug. 4, 2016, and entitled "An Endograft For Treating Branched Vessels," the entire contents of each of which are incorporated herein by reference.

TECHNICAL FIELD

The present disclosure relates generally to medical devices. More particularly, the present disclosure relates to endografts. In particular, the present disclosure relates to endografts deployable into the vascular system of humans or animals.

BACKGROUND

Endografts and delivery device assemblies for endografts are used in aortic intervention. They are used by vascular surgeons to treat aneurysms and to repair regions of the aorta, including the aortic arch, the thoracic aorta, the abdominal aorta and the aortic bifurcation.

Multiple stent grafts may be implanted to provide a system of interconnected stent grafts. Interconnected stent grafts can be made of fenestrated stent grafts and smaller side branch grafts.

Endografts for treating branched vessels, typically stent grafts, are intricate and take considerable time to produce. There is thus a need to provide an improved endograft for treating branched vessels.

Throughout this specification, the term "distal" with respect to a portion of the aorta, a deployment device or an endograft means the end of the aorta, deployment device or endograft further away in the direction of blood flow from the heart and the term "proximal" means the portion of the aorta, deployment device or end of the endograft nearer to the heart in the direction of blood flow. When applied to other vessels, similar terms such as caudal and cranial should be understood.

SUMMARY

According to a first aspect of the present disclosure, there is provided an endograft comprising a proximal end and a distal end, the endograft comprising a tube of biocompatible material, the tube comprising: a main lumen extending longitudinally from the proximal end to the distal end, the main lumen including a proximal portion, an intermediate portion and a distal portion; a branch lumen within the intermediate portion of the main lumen; and a seam, the seam extending longitudinally beside both the branch lumen and the distal portion of the main lumen, wherein the tube comprises a lateral cross-section defining a tubular wall pinched together by the seam to form a branch portion.

According to a second aspect of the present invention, there is provided a method of producing a endograft comprising the steps of: providing a tube of biocompatible material, the tube having a tubular wall; flattening the tube so that the tubular wall forms two substantially planar wall portions; partitioning the flattened tube by creating a longitudinal seam between the two wall portions; cutting a piece out of the tube from a position adjacent to the longitudinal seam so as to create a branch mouth into the tube; attaching a super-elastic ring to the branch mouth; and everting the tube.

BRIEF DESCRIPTION OF DRAWINGS

Embodiments of the present disclosure will be discussed with reference to the accompanying drawings wherein:

FIG. 5A shows an endograft according to the disclosure is an isometric view;

FIGS. 5B, 5C and 5D show lateral cross-sections of the endograft of FIG. 5A through section lines 5B-5B, 5C-5C and 5D-5D respectively;

FIG. 7 is an isometric view looking into the endograft of FIGS. 5A and 6 from its proximal end;

FIG. 8 is an isometric view of a space frame;

FIG. 9 is an isometric view showing the space frame of FIG. 8 attached to a portion of the endograft of FIG. 4A;

DESCRIPTION OF EMBODIMENTS

Figure 1:
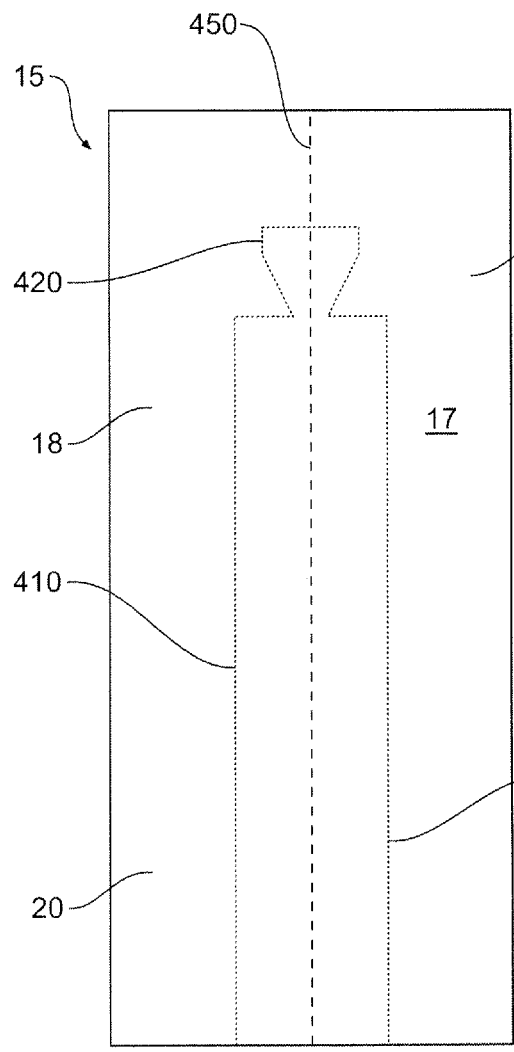
FIG. 1 is a plan view of a flattened tube of biocompatible material with a 12 o'clock line down its centre.

One example of an endograft 10 according to the present disclosure is shown in FIG. 5A. FIGS. 5B, 5C and 5D show lateral cross-sections of the endograft of FIG. 5A through section lines 5B-5B, 5C-5C and 5D-5D respectively.

Referring to FIG. 5A, it can be seen that the endograft 10 consists generally of in the form of a tubular stent graft having a proximal end portion 12 and a distal end portion 14, a tubular body 15, and a lumen 16 extending therethrough. The endograft 10 may be configured to receive a fluid flow in a proximal to distal direction.

The endograft 10 may be any suitable length. In one example, the endograft 10 is a suitable length corresponding to the length of a lesion site where the endograft 10 is to be positioned.

The endograft 10 may be in a compressed or collapsed configuration (not shown) or a radially expanded configuration (shown in FIG. 5A). In the expanded configuration the endograft 10 may apply a radially outward force upon at least a portion of a vessel, duct, or lumen e.g., to maintain patency within a passageway.

The endograft 10 may be any suitable selected diameter and may be constructed or any biocompatible graft material 20 which is suitable for facilitating repair of an injured or diseased body vessel. The graft material 20 may be synthetic and/or naturally-derived material. Synthetic biocompatible polymers may include but are not limited to polyethylene terephthalate, polyurethane, nylon, polyester, high molecular weight polyethylene (such as Thoralon), polytetrafluoroethylene, or combinations thereof. The graft material 20 can be porous or non-porous and also may be impregnated or coated with one or more therapeutic substances. In one example, the graft material may be constructed of the commercially available material referred to as Dacron. In another example the graft material may consist of small-intestine submucosa ("SIS") material, which may be obtained from porcine intestine. The graft material should have sufficient flexibility to allow for navigation of the vasculature and delivery to a targeted area in the body. Preferably, the graft material 20 is a low profile material or an ultralow profile material.

The endograft 10 may be supported by one or more stents 21 along its length. One or more stents 21 may be located on an interior surface 23, exterior surface 25, or both, of the tubular body 15 of the endograft 10. The number of stents and their placement (internal or external) can be varied to suit the particular application or patient anatomy. Alternatively, the endograft 10 may be unsupported along its length such that there are no body stents located on the graft material between the proximal end portion 12 and distal end portion 14 of the endograft 10.

In one example, stent 21 may be a Z-stent. For example, stent 21 may have a distal end 30 with a series of distal apices 31 and a proximal end 39 with a series of proximal apices 33. Stent 21 may also have one or more elongate struts 35 connecting the distal apices 31 to the proximal apices 33.

Suitable stents 21 for use in connection with the endograft 10 described herein may be self-expanding or mechanically-expandable stents or both, and may be deployed according to conventional methodology. A self-expanding stent may be manufactured from a shape-memory alloy, such as nickel titanium alloy (Nitinol). If the stent comprises a self-expanding material such as Nitinol, the stent may be heat-set into the desired expanded state whereby the stent can assume a relaxed radially expanded configuration. The stent may be made from other metals and alloys that allow the stent to return to its original expanded configuration upon deployment, such as, for example, stainless steel, cobalt-chrome alloys, amorphous metals, and/or non-metallic materials as would be recognized by one of skill in the art. Additionally or alternatively, the endograft 10 may be mechanically expanded, such as through the use of an expandable balloon placed within the lumen 16 of the endograft 10 and then radially outwardly expanded.

In the example shown in FIG. 5A, a plurality of zig zag stents 21 include a proximal end internal stent 13 and a distal end internal stent 27. Between stents 13 and 27 they may be three external stents 22, 24, 26.

The endograft 10 may be anchored to an interior wall of a body vessel, duct, or lumen proximally and/or distally to a lesion site. The endograft 10 of FIG. 5A has a proximal end sealing region 11 and a distal end sealing region 29. For example, the distal sealing region 29 of the endograft 10 of FIG. 5A may include an uncovered distal stent 28. This distal stent 28 may include barbs (not shown) to anchor the endograft 10 in place.

The tubular body 15 of the endograft 10 may have a tubular wall 17 extending from the proximal end portion 12 to the distal end portion 14 of the endograft 10. The diameter of the tubular body 15 may change along the length of the endograft 10. In one example, the diameter at the proximal end portion 12 of the tubular body 15 is greater than the diameter at the distal end portion 14 of the tubular body 15. A tapered transition portion 45 may connect the proximal end portion 12 and the distal end portion 14.

The tubular body 15 may have one or more lumens extending therethrough. In one example, the tubular body 15 comprises a main lumen 16 extending longitudinally from the proximal end portion 12 to a distal end portion 14 of the endograft 10.

The endograft 10 may include an internal branch portion 37. In one example, the internal branch portion 37 extends from a recess or opening 250 in the tubular wall 17 into the main lumen 16 of the tubular body 15. The branch portion 37 may have a proximal end 52, and distal end 54 and a lumen 36 extending therethrough. In one example, the proximal end 52 has a larger diameter than the distal end 54 of the branch portion 37. The branch portion 37 may be constructed from the same biocompatible material as the graft material 20.

FIGS. 5B, 5C, and 5D show the endograft 10 at the proximal lateral 100, intermediate lateral 200 and distal lateral 300 cross-sections, respectively. These lateral cross-sections can be identified as section lines 5B-5B, 5C-5C and 5D-5D marked on FIG. 5A respectively. As shown in FIG. 5B, the tubular wall has a main lumen 16 extending therethrough at the proximal lateral portion 100 of the endograft 10. In the intermediate lateral 200 cross section (shown in FIG. 5C), the main lumen 16 and the lumen 36 of the internal branch portion 37 extend through the tubular body 15. FIG. 5C also shows a seam 40 in the graft material 20 which will be described in greater detail below. In the distal lateral 300 cross-section (FIG. 5D), the main lumen 16 extends through the endograft 10.

In order to better understand the structure and construction of the endograft shown in FIGS. 5A to 5D, one method of constructing the endograft 10 shown in FIG. 5A will now be described with reference to FIGS. 1-4. In particular, one novel feature of the disclosed endograft 10 is that the internal branch portion 37 is constructed using the excess of the graft material 20 used to make the tubular body 15, thus eliminating or reducing the need to sew a separate branch to the graft material.

Figure 2:
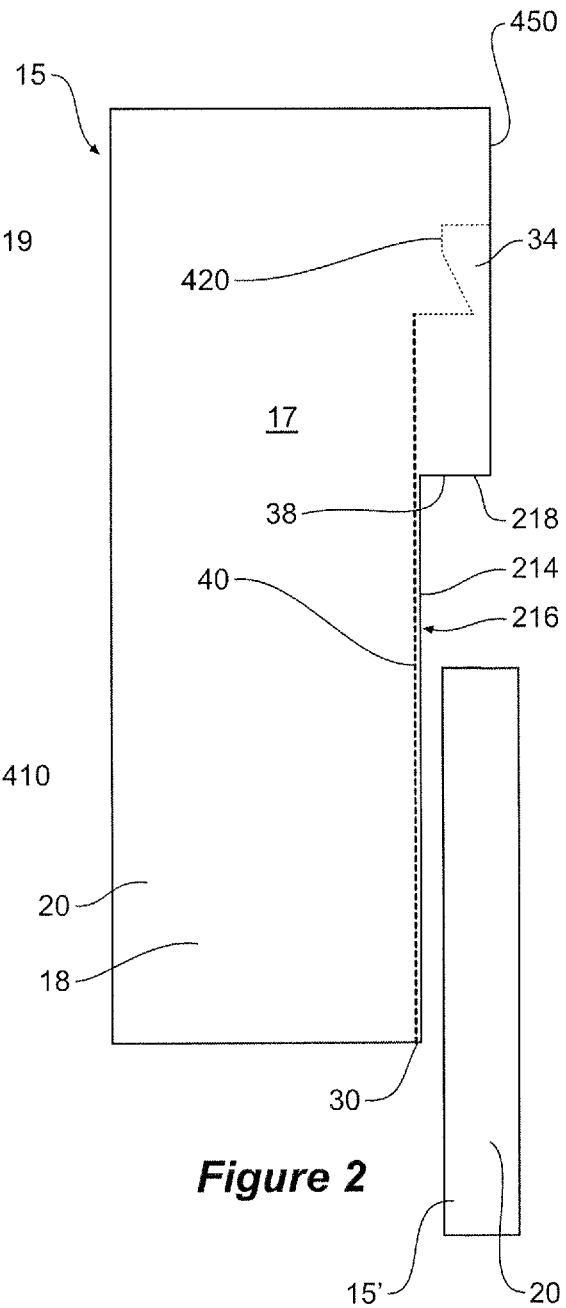
FIG. 2 is a similar view to that of FIG. 1 but shows the 12 o'clock line on the right hand lateral edge of the tube.

FIG. 1 is a plan view of a flattened tube of biocompatible material with a 12 o'clock line down its centre. FIG. 2 is a similar view to that of FIG. 1 but shows the 12 o'clock line on the right hand lateral edge of the tube.

Referring to FIG. 1, a tube of biocompatible material that may form the tubular body 15 is shown. In particular, tubular wall 17 of the endograft 10 is shown in a flattened condition so as to form two parallel spaced-apart folds that define tubular wall portion 18 and tubular wall portion 19. Referring to FIG. 1, a 12 o'clock line 450 is marked on the graft material 20. Further lines 410 and 420 are marked on the graft material 20. Lines 410 and 420 may represent a portion of the outline of the internal branch portion 37. The line 420 indicates the position that will become the recess or opening 250 and the exit 34 from the branch lumen 36.

FIG. 2 shows the graft material 20 folded at the 6 and 9 o'clock position aligning the lines 410 with each other.

As shown in FIG. 2, the flattened graft material may be partitioned by sewing a seam 40 along the internal branch lines 410. In other words, a seam 40 may attach two portions of the graft material 20 together along line 410. The seam 40 may be sewn using any suitable method and may be sewn using any suitable biocompatible material.

After the seam 40 is sewn, an excess portion 15' of graft material 20 may be cut out and discarded. In one example, a longitudinal cut may occur near the seam 40 at longitudinal edges 214 and 216. Two adjacent longitudinal edges 214 and 216 may join each other along the seam 40. A latitudinal cut may occur at lateral edge 218.

The graft material 20 may be sealed my any means along one or more cut lines. In one example (shown in FIG. 3b), the graft material 20 is heat sealed along longitudinal edges 214 and 216 as described below.

The seam 40 may extend from the distal end portion 30 of the endograft 10 to a point proximal to the lateral edge 218. A branch portion 37 may be formed in the tubular wall 17 area between the seam 40 and the 12 o'clock line 450. The branch portion 37 may have a mouth 38 and an exit 34 that connects the branch portion 37 to the tubular body 15.

Figure 3A:
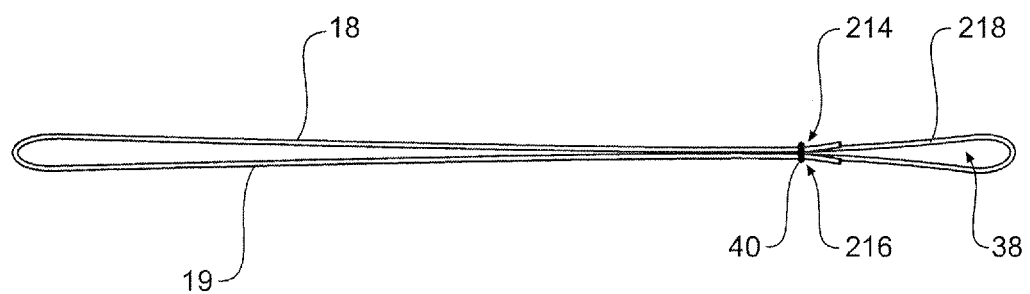
FIG. 3A is an end view of the tube of FIG. 2 after a longitudinally extending portion from the tubular wall has been cut out.
Figure 3B:
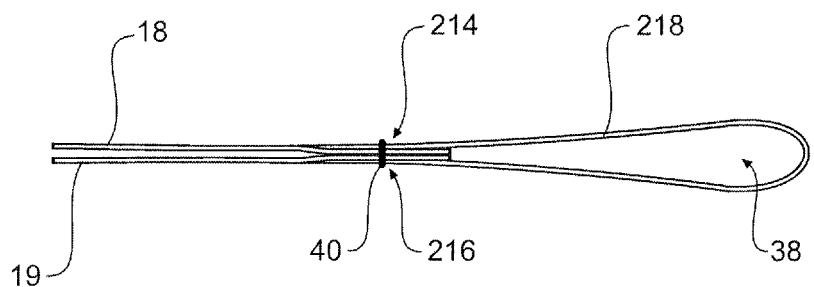
FIG. 3B is similar view to FIG. 3A but shows the tube after edges formed from a cut have been sealed.

FIGS. 3A and 3B show end views of the flattened tube of FIG. 2 after a seam 40 has been sewn and a portion 15' of the graft material 20 has been cut out and discarded. In particular, FIG. 3A is an end view of the tube of FIG. 2 after a longitudinally extending portion from the tubular wall has been cut out. FIG. 3B is a similar view to FIG. 3A but shows the tube after edges 214 and 218 formed from a cut have been heat sealed.

As shown in FIGS. 3A and 3B, the tubular wall portions 18 and 19 are sewn together to form the seam 40. Adjacent longitudinal edges 214 and 216 join each other at a lateral edge 218. All of the edges 214, 216 and 218 are formed when the excess graft material 15' is cut and discarded. This leaves a lateral edge 218 and the mouth 38 of the internal branch portion 37.

Figures 4A, 4B, 4C, 4D:
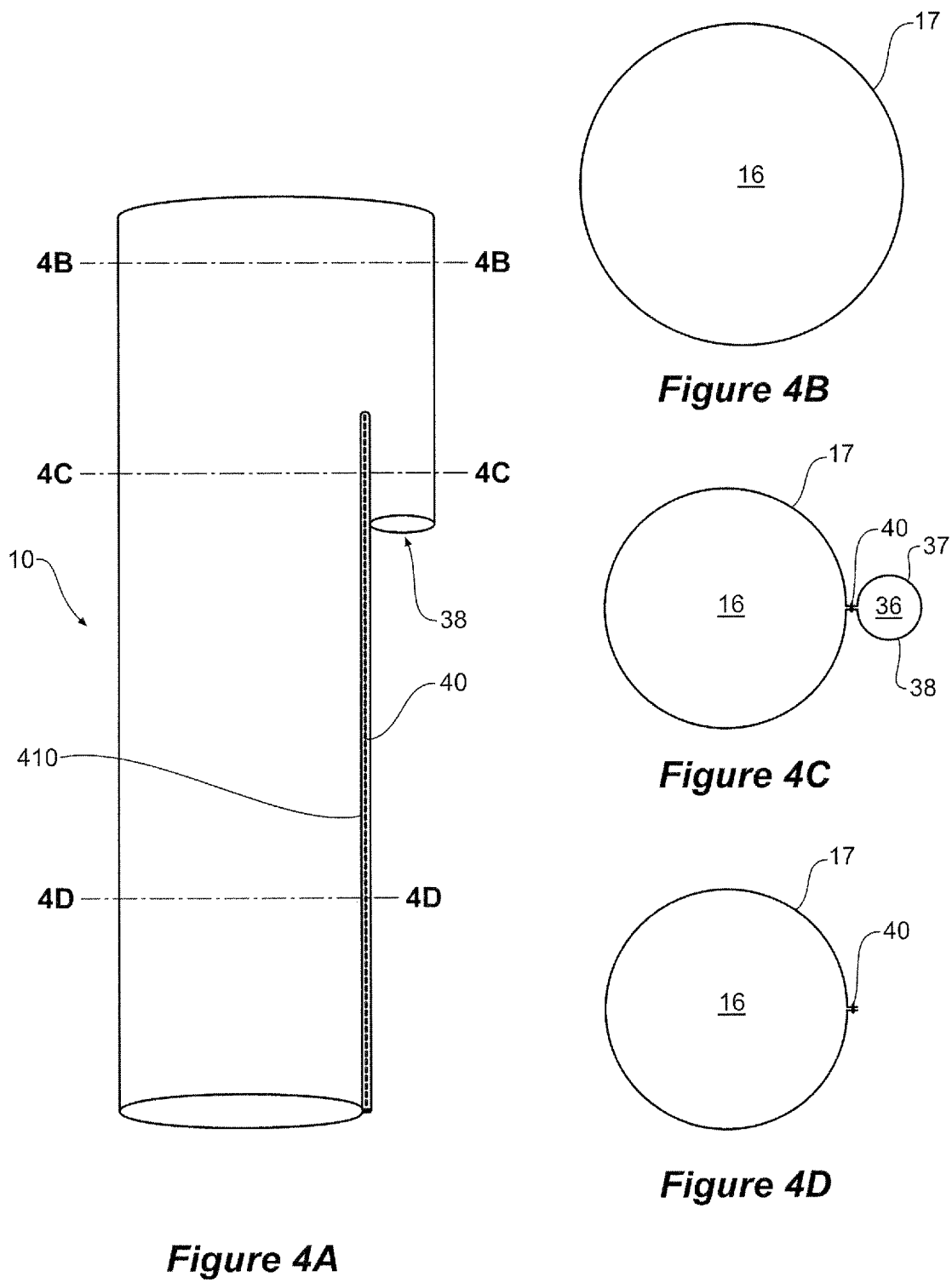
FIG. 4A is an isometric view showing the tube of FIG. 3.
FIGS. 4B, 4C and 4D are proximal lateral, intermediate lateral and distal lateral cross-sections through the tube shown in FIG. 4A through section lines 4B-4B, 4C-4C and 4D-4D respectively.

FIG. 4A is an isometric view showing the tube of FIG. 3B. As shown in FIG. 4A, the graft material 20 is no longer in a flattened configuration, but rather in a tubular configuration. The seam 40 occurs along the graft material 20 along line 410 and the excess graft material has been cut away. The mouth 38 to the internal branch portion 37 is illustrated in FIG. 4A.

FIGS. 4B, 4C and 4D are proximal lateral, intermediate lateral and distal lateral cross-sections through the tube shown in FIG. 4A through section lines 4B-4B, 4C-4C and 4D-4D respectively. As shown in FIG. 4B, the graft material forms a tubular wall 17 with main lumen 16. At the intermediate lateral cross-section, FIG. 4C illustrates addition of the branch portion 37 having a lumen 36. FIG. 4C also shows the seam 40 in the tubular wall 17. At the distal lateral cross section 4D-4D shown in FIG. 4D, the tubular wall 17 and the seam 40 are illustrated.

It may be desirable to provide additional support to the internal branch portion 37. In one example, a super-elastic ring of nitinol wire is attached to support the branch portion 37. For example, space frame 41 may provide additional support to the internal branch portion 37. FIG. 8 is an isometric view of a space frame. FIG. 9 is an isometric view showing the space frame of FIG. 8 attached to the internal branch portion 37 shown in FIG. 4A.

As shown in FIGS. 8 and 9, it can be seen that the branch portion 37 may have a space frame 41. The space frame 41 may have an entrance reinforcing ring 43 and an exit reinforcing ring 47. The entrance and exit reinforcing rings 43,47 may be spaced apart axially by one or more struts 44 and 48. In one example, the space frame 41 comprises an assembly of two individual ring and strut components 42, 46. Each ring and strut component 42, 46 may comprise a circular ring portion defining a plane of the circular ring portion and a strut extending at right angles to the plane of the circular ring portion from a periphery of the circular ring portion. One of the two circular rings may form the entrance reinforcing ring 43 and the other of the two circular rings may form the exit reinforcing ring 47. For instance, ring and strut component 42 may comprise the entrance reinforcing ring 43 and the strut 44. Ring and strut component 46 may comprise the exit reinforcing ring 47 and strut 48.

As shown in FIG. 9, the space frame 41 may be attached to the branch portion 37 in any suitable way. In one example, space frame 41 is sewn into the branch portion 37 with stitching 49. The mouth 38 of the branch portion 37 may be biased towards an open condition by the entrance reinforcing ring 43. Similarly, the exit reinforcing ring 47 may bias the exit 34 (shown FIG. 6) into an open condition. This open condition is also apparent in the isometric view of FIG. 7 looking down into the endograft 10 from its proximal end 12.

The space frame 41 may be constructed with any biocompatible material. In one example, the space frame 41 comprises super-elastic wire, such as Nitinol. Other suitable materials may be used.

The tubular body 15 graft material 20 shown in FIGS. 1-4 and 8-9 may be everted or turned inside out so that the branch portion 37 sits internally in the tubular body 15, as shown in the endograft 10 shown in FIGS. 5-7 and 10-11. FIGS. 5A-D show one example of an endograft 10 after it has been constructed according to the disclosure above.

Returning to FIGS. 5A-D, once the tubular body 15 graft material 20 is turned inside out, stents 13, 22, 24, 26, 28, and 29 may be attached to the tubular wall 17 by any known method including using adhesives and stitching. Once the branch portion 37 is located internally in the tubular body, the shape of the branch portion 37 may further be changed as desired. For example, the branch portion 37 may be further cut and heat sealed to any desirable shape. In one example, excess tubular wall material may be cut out and the resultant slits may be sewn to form seams 272 and 274. In other words, the excess material may be gathered and trimmed to create a V-shape (as shown in FIG. 5A).

As shown in FIG. 5A, the recess or opening 250 in the tubular wall 17 may open into the exit 34 of the branch portion 37. The recess or opening 250 may be at least partially disposed within a V-shaped region 260 formed between two adjacent struts 22a, 22b and a bend 22c of zig zag stent 22, that stent 22 being one of the plurality of zig zag stents 21 as is shown most clearly in FIG. 5A. In one example, the tubular wall 17 of the main lumen may have at least one seam 40 adjacent to the V-shaped region 260 formed between two adjacent struts and a bend of one of the plurality of zig zag stents 21.

As shown in FIG. 5A, the tubular body 15 of the endograft 10 may include a proximal portion 100, an intermediate portion 200 and a distal portion 300. The tubular body 15 of the endograft 10 may have a seam 40 extending longitudinally along a portion of the tubular wall 17.

FIGS. 5B, 5C and 5D show lateral cross-sections of the endograft of FIG. 5A through section lines 5B-5B, 5C-5C and 5D-5D respectively. In the proximal portion (shown in FIG. 5B), the tubular wall 17 has a main lumen 16. In the intermediate portion 200 (shown in FIG. 5C) the internal branch portion 37 and the branch lumen 38 may be within the main lumen 16. Referring again to FIGS. 5A, 5B, 5C, 5D and 6, it can be seen that a seam 40 may be created where the tubular wall 17 is pinched together to form a branch portion 37. In the distal portion (shown in FIG. 5D), the distal end 14 of the endograft can be seen as well as the seam 40 formed where the tubular wall 17 is stitched after the excess graft material has been cut out and discarded.

Figure 6:
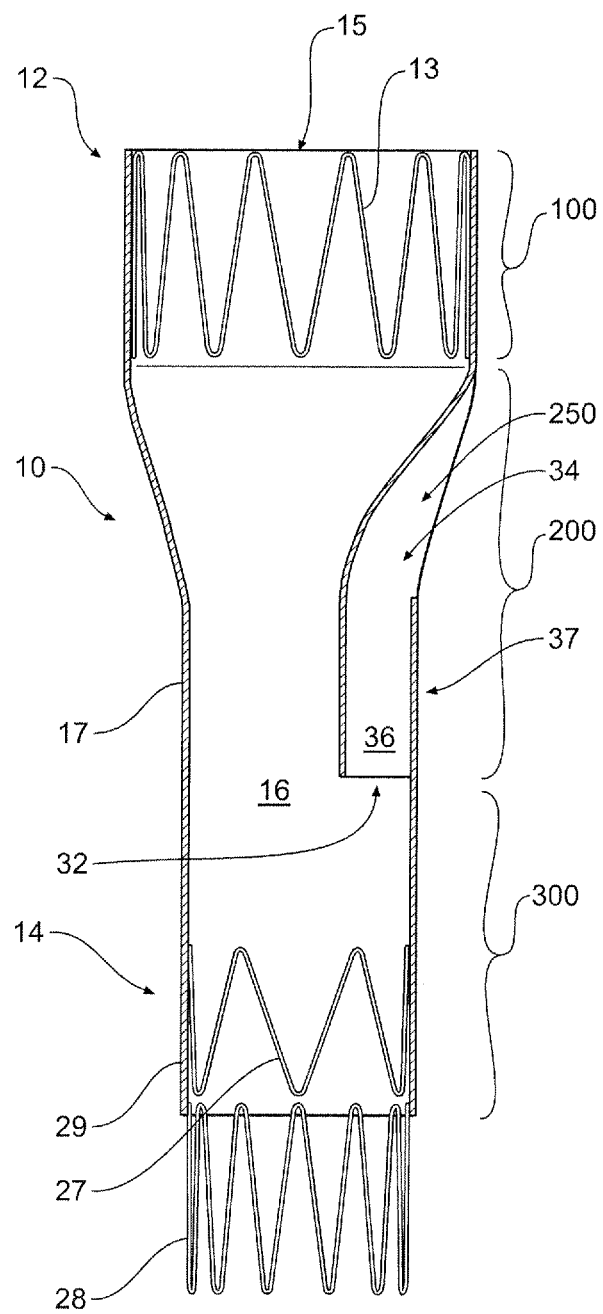
FIG. 6 is a longitudinal cross-sectional view of the endograft of FIG. 5A.

FIG. 6 is a longitudinal cross-sectional view of the endograft of FIG. 5A. FIG. 7 is an isometric view looking into the endograft of FIGS. 5A and 6 from its proximal end.

Referring to the longitudinal cross-sectional view of FIG. 6, the internal branch portion 37 can be seen internal to the tubular body 15. With this cross-sectional view, the external stents 22,24,26 and the wires of the space frame 41 are not shown (the space frame 41 is shown in FIG. 8 and is described below).

The branch portion 37 comprises an entrance 32 into the main lumen 16 within the intermediate portion 200 of tubular body 15. The branch portion 37 may have an exit 34 through the tubular wall 17 of the tubular body 15. The exit 34 through the tubular wall of the main lumen 16 may open into the recess or opening 250. A lumen 16 may run between the entrance 32 and the exit 34.

Referring now to FIG. 7, which is an isometric view looking down into the endograft 10 from its proximal end 12, the branch portion 37 can be seen within the main lumen 16. The proximal end of the branch portion 37 may have a larger diameter than the distal end of the branch portion 37.

The deployment of one embodiment of the endograft 10 can occur in any vessel, duct, or lumen. The endograft 10 may be deployed in a patient using any known technique or method. In one example, the deployment device is the device disclosed in U.S. Pat. No. 7,537,606 titled Branch stent graft deployment and method, which is herewith incorporated in its entirety into this specification.

Figure 10A:
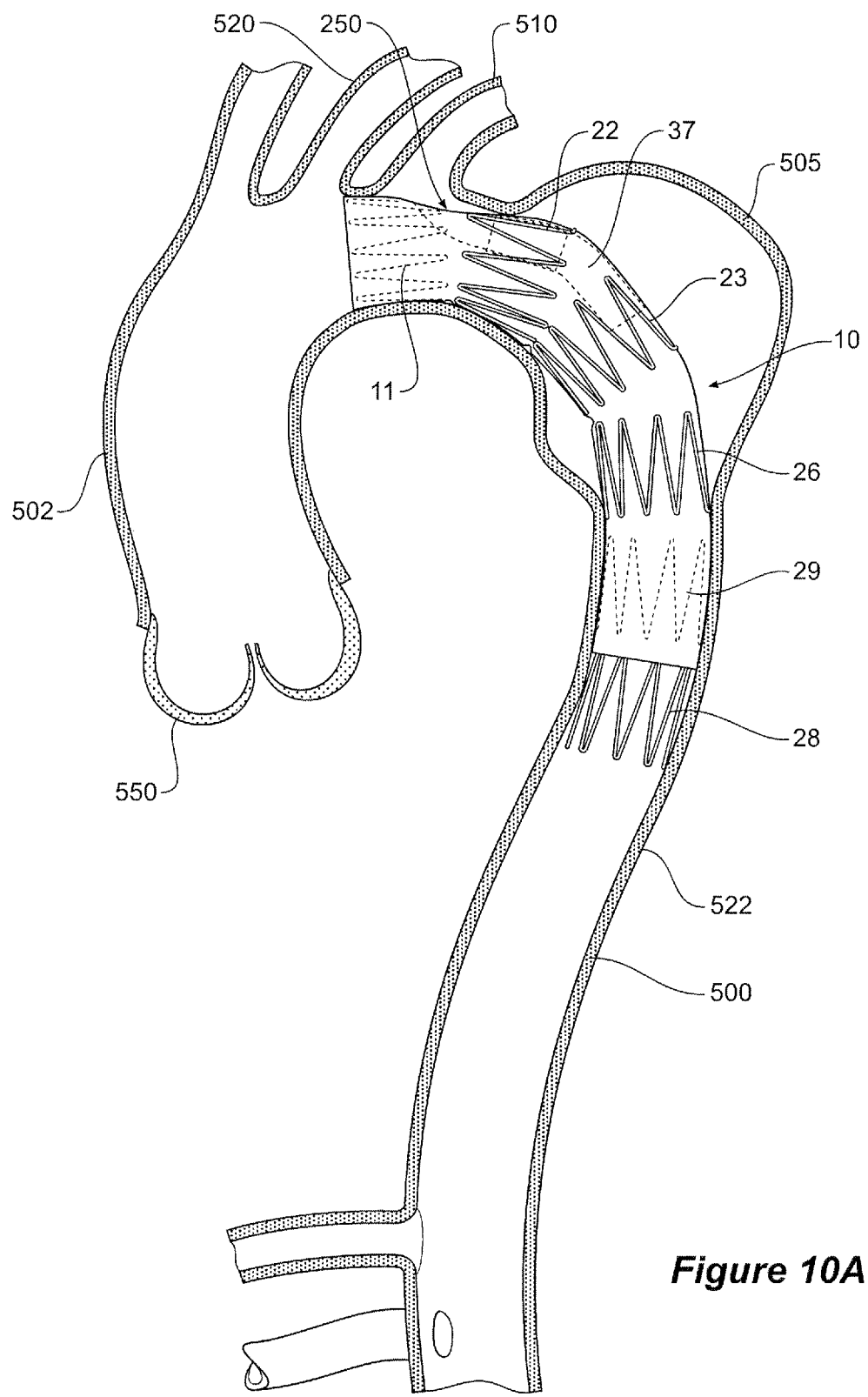
FIG. 10A is a diagrammatic view of the endograft of FIGS. 5A, 6 and 7 within the anatomy of a patient.
Figure 10B:
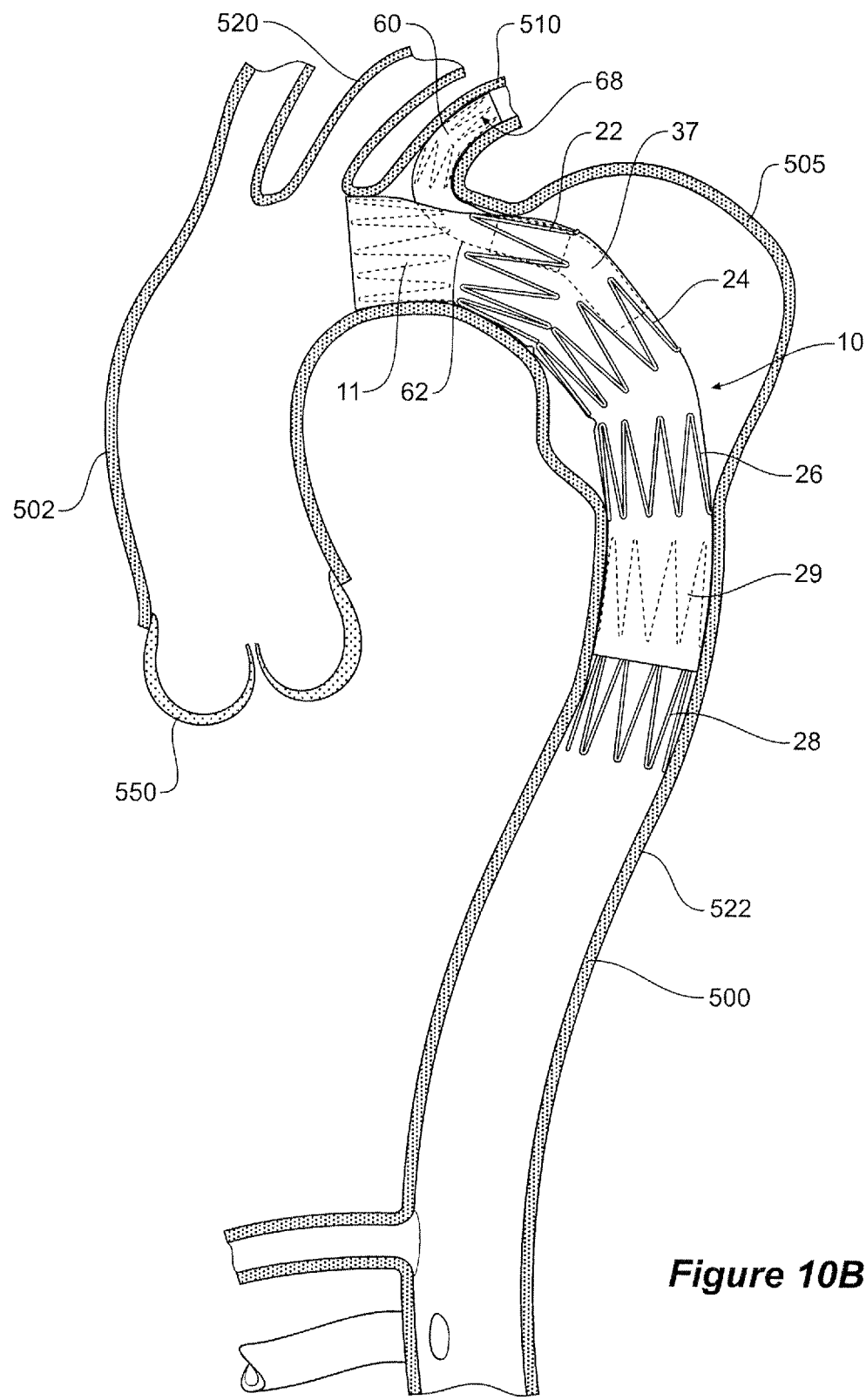
FIG. 10B is a similar view to that of FIG. 10A but also shows a side branch endograft.

In one example, endograft 10 can be deployed into the thoracic arch of a patient. FIG. 10A is a diagrammatic view of the endograft of FIGS. 5A, 6 and 7 within the anatomy of a patient. FIG. 10B is a similar view to that of FIG. 10A but also shows a side branch endograft.

The thoracic arch region of a patient generally comprises an ascending aorta 502 extending from an aortic valve 550 of the heart of the patient, then over the thoracic arch to the descending aorta 522. From the thoracic arch, three main arteries extend. These are the innominate artery, the left carotid artery 520 and a subclavian artery 510. This embodiment of the disclosure will generally be discussed with reference to deployment of an endograft 10 in the form of a stent graft 10 with a side branch into the aorta 500 and left subclavian artery 510 but the disclosure is not so restricted.

The endograft 10 may be necessary in the aortic arch region when an aneurysm in the aorta 500 extends up the aorta 500 to such an extent that there is insufficient patent aortic wall to provide good sealing for a stent graft 10 distally of the left subclavian artery 510 (for instance, see aneurysmal portion 505 in FIG. 10A). It is desirable in such circumstances to extend the stent graft 10 to seal onto good artery wall at least between the left carotid artery 520 and the left subclavian artery 510.

The proximal end sealing region 11 is shown in FIGS. 10A and 10B sealing onto good artery wall at least between the left carotid artery 520 and the left subclavian artery 510. The distal end sealing region 29 is also shown in FIGS. 10A and 10B sealing onto good artery wall along the descending aorta 522 below the aneurysmal portion 505.

FIG. 10A shows a detailed view of the deployed stent graft 10, as shown in FIG. 5A, into a thoracic arch of a patient. A separate balloon expandable, or self expanding, side arm or side branch endograft 60 such as stent graft 60 can then be deployed brachially through the subclavian artery 510 so that its upstream or proximal end enters the branch lumen 36 and then it can be allowed to expand, or be balloon expanded, so that the proximal end is expanded within the branch portion 37 to seal the side branch stent graft 60 into the branch lumen 36 of the main stent graft 10, as is shown in FIG. 10B. In other words, the recess or opening 250 may be adapted to accommodate a side arm, the side arm having an upstream end and a downstream end, the upstream end positionable within the branch lumen and the downstream end within a branch vessel. Again, this can be achieved as is described in the afore-mentioned U.S. Pat. No. 7,537,606 titled Branch stent graft deployment and method.

Figure 11:
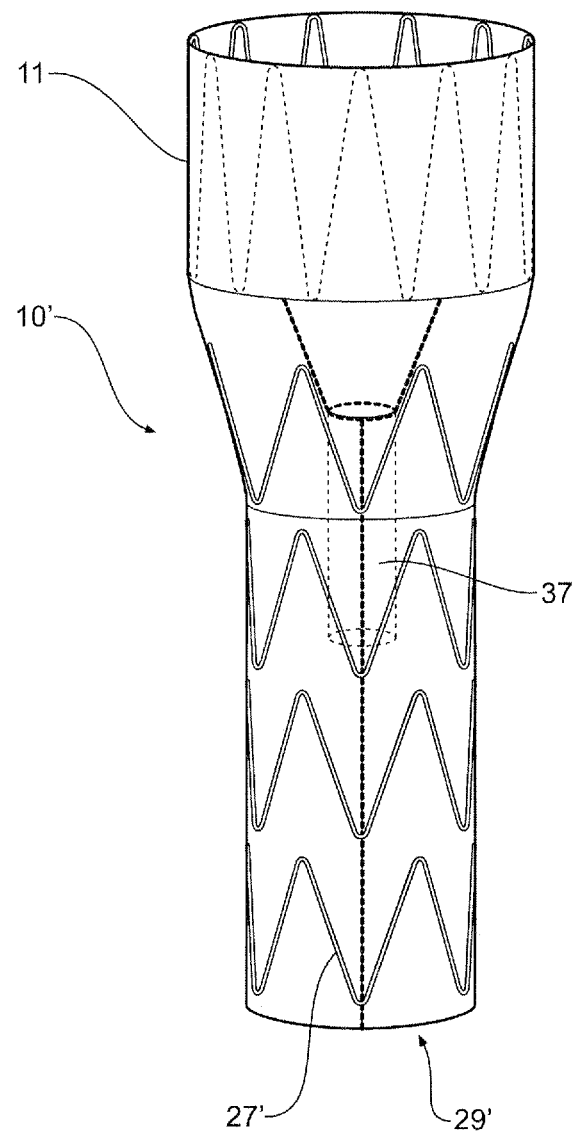
FIG. 11 is an isometric view of an alternative endograft according to the disclosure.

FIG. 11 is an isometric view of an alternative endograft 10' according to the disclosure. With this embodiment, the distal most stent 27' is an external stent. That is, the stent 27' is secured on the outside of the tubular body 15. This endograft 10' can be used as part of an interconnected stent graft assembly where a more distal stent graft seals to the inside of the distal end of the endograft 10'. Such an arrangement may be suitable for a patient who has an aneurysm that extends further down the descending aorta that the aneurysm 505 shown in FIGS. 10A and 10B.

The above described method of producing the endograft 10 utilises excess graft material 20 to produce the branch portion 37. This eliminates the need to separately fabricate and attach the branch portion 37, reducing the complexity of the final endograft 10 or endograft 10', as illustrated in FIGS. 5A and 11 respectively.

The disclosure is not limited to this particular application but is discussed in relation to this particular application as an example.

Embodiments of the disclosure will be used by vascular surgeons to treat aneurysms and to repair regions of the aorta, including, but not limited to, the aortic arch. Embodiments of the disclosure will be used in other parts of the vasculature system.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the disclosure is not restricted in its use to the particular application described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope of the disclosure as set forth and defined by the following claims

The invention claimed is:

1. An endograft comprising a proximal end and a distal most end, the endograft comprising a tube of biocompatible material and having a graft material wall, the tube comprising:
    a main lumen extending longitudinally from the proximal end to the distal most end, the main lumen including a proximal portion, an intermediate portion and a distal portion;
    a branch within the intermediate portion of the main lumen having a proximal opening a distal opening and a branch lumen; and an internal stitched seam, the stitched seam extending longitudinally beside both the branch lumen and from the proximal opening of the branch to the distal most end of the endograft, wherein the tube comprises a lateral cross-section defining a tubular wall, wherein a portion of the tubular wall is pinched together at the seam to form the branch.

2. The endograft as claimed in claim 1 wherein the branch distal opening is within the main lumen and faces the distal opening of the endograft, and the branch proximal opening opens externally through the tubular wall of the main lumen and faces the proximal end of the endograft.

3. The endograft as claimed in claim 2 comprising a recess in the graft material wall, wherein the proximal opening opens up into the recess externally of the main lumen.

4. The endograft as claimed in claim 3 wherein the tube is supported by a plurality of zig zag stents, each of the stents comprising a plurality of struts and bends, the bends being between adjacent struts, wherein the recess is at least partly disposed within a V-shaped region formed between two adjacent struts and a bend of one of the plurality of zig zag stents.

5. The endograft as claimed in claim 4 wherein the tubular wall of the main lumen comprises at least one seam adjacent the V-shaped region formed between two adjacent struts and a bend of one of the plurality of zig zag stents.

6. The endograft as claimed in claim 3 wherein the recess is configured to receive a side arm, the side arm having an upstream end and a downstream end, the upstream end positionable within the branch lumen and the downstream end positionable within a branch vessel.

7. The endograft as claimed in claim 2 wherein the branch comprises a reinforcing ring about the proximal opening.

8. The endograft as claimed in claim 7 wherein the branch comprises a reinforcing ring about the distal opening.

9. The endograft as claimed in claim 1, wherein the branch comprises a reinforcement in the form of a space frame.

10. The endograft as claimed in claim 9 wherein the space frame comprises an assembly of a first ring and strut component and a second ring and strut component separate from the first ring and strut component, wherein each of the first and second ring and strut components has a circular ring defining a plane and a strut extending at right angles to the plane of the circular ring from a periphery of the circular ring portion, whereby one of the two circular rings forms the entrance reinforcing ring and the other of the two circular rings forms the exit reinforcing ring.

11. The endograft as claimed in claim 9 wherein the space frame comprises super-elastic wire.

12. The endograft as claimed in claim 11, wherein the super-elastic wire of the space frame comprises nitinol.

13. An endograft comprising a proximal end, a distal most end and a longitudinal axis, the endograft comprising a tube of biocompatible material, the tube comprising:

a main lumen extending longitudinally from the proximal end to the distal most end, the main lumen including a proximal portion, an intermediate portion and a distal portion;

a branch within the intermediate portion of the main lumen having a proximal opening, a distal opening, and a branch lumen; and a stitched seam, the stitched seam extending longitudinally beside both the branch lumen and from the proximal opening of the branch to the distal most end of the endograft, wherein the tube comprises a lateral cross-section defining a tubular wall, wherein a portion of the tubular wall is pinched together at the stitched seam to form the branch, wherein the proximal opening opens to an exterior of the endograft and the distal opening of the branch is within the main lumen of the endograft, and both the proximal and distal openings are substantially perpendicular to the longitudinal axis.

14. An endograft comprising a proximal end, a distal end, a longitudinal axis, and having a first configuration and a second implantable configuration, the endograft comprising a tube of biocompatible material, the tube comprising:

a main lumen extending longitudinally from the proximal end to the distal end, the main lumen including a proximal portion, an intermediate portion and a distal portion;

a branch disposed at the intermediate portion of the main lumen having a proximal opening, a distal opening, and a branch lumen; and a stitched seam, the stitched seam extending longitudinally beside both the branch lumen and from the proximal opening of the branch to the distal most end of the endograft, wherein the tube comprises a lateral cross-section defining a tubular wall, wherein a portion of the tubular wall is pinched together by a seam to form the branch, wherein in the first configuration the branch is external of the main lumen and the proximal opening is within the main lumen, and in the second implantable configuration the branch is within the main lumen and the proximal opening opens to an exterior of the endograft and the distal opening of the branch is within the main lumen of the endograft.

* * * * *